United States Patent
Zappacosta et al.

(10) Patent No.: US 11,419,641 B2
(45) Date of Patent: *Aug. 23, 2022

(54) SPINOUS PROCESS FIXATION SYSTEM AND METHODS THEREOF

(71) Applicant: GLOBUS MEDICAL, INC., Audubon, PA (US)

(72) Inventors: Jason Zappacosta, Philadelphia, PA (US); Aditya Ingalhalikar, Pune MH (IN); Don Reed, Philadelphia, PA (US); Robert Rightler, Pennsburg, PA (US); Darren Clutter, Barto, PA (US)

(73) Assignee: Globus Medical Inc., Audubon, PA (US)

( * ) Notice: Subject to any disclaimer, the term of this patent is extended or adjusted under 35 U.S.C. 154(b) by 167 days.

This patent is subject to a terminal disclaimer.

(21) Appl. No.: 16/892,393

(22) Filed: Jun. 4, 2020

(65) Prior Publication Data
US 2020/0297392 A1    Sep. 24, 2020

Related U.S. Application Data

(63) Continuation of application No. 15/634,273, filed on Jun. 27, 2017, now Pat. No. 10,695,106, which is a (Continued)

(51) Int. Cl.
*A61B 17/70* (2006.01)
*A61B 17/56* (2006.01)
*A61B 17/00* (2006.01)

(52) U.S. Cl.
CPC ...... *A61B 17/7068* (2013.01); *A61B 17/7065* (2013.01); *A61B 17/7067* (2013.01); (Continued)

(58) Field of Classification Search
CPC .................. A61B 17/7067; A61B 17/7068
See application file for complete search history.

(56) References Cited

U.S. PATENT DOCUMENTS

| 8,114,136 B2 | 2/2012 | Carls et al. |
| 8,241,329 B2 | 8/2012 | Abdou |

(Continued)

FOREIGN PATENT DOCUMENTS

| WO | 2014159788 A1 | 10/2014 |
| WO | 2015058193 A1 | 4/2015 |

*Primary Examiner* — Jan Christopher L Merene

(57) ABSTRACT

An implantable device may be provided. The implantable device may comprise an upper assembly comprising a ramped base and a pair of opposing windows. The pair of opposing windows may extend upward from either lateral side of the ramped base. A gripping assembly may be disposed in each window. The implantable device may further comprise a lower assembly comprising a ramped base and a pair of opposing windows. The pair of opposing windows may extend down from either lateral side of the ramped base. A gripping assembly is disposed in each window. The implantable device may further comprise a ramped actuator assembly disposed between the upper assembly and the lower assembly. The ramped actuator may be configured to transition the implantable device from a collapsed form having a first height to an expanded form having a second height and wherein the second height is greater than the first height.

18 Claims, 11 Drawing Sheets

Related U.S. Application Data continuation of application No. 15/364,855, filed on Nov. 30, 2016, now Pat. No. 9,724,134, which is a continuation of application No. 14/989,919, filed on Jan. 7, 2016, now Pat. No. 9,539,032, which is a continuation of application No. 14/090,780, filed on Nov. 26, 2013, now Pat. No. 9,259,249.

(52) U.S. Cl.
CPC ............ *A61B 2017/00991* (2013.01); *A61B 2017/564* (2013.01); *Y10T 29/49826* (2015.01)

(56) References Cited

U.S. PATENT DOCUMENTS

| | | | |
|---|---|---|---|
| 9,301,788 B2* | 4/2016 | Wolters | A61B 17/7065 |
| 2006/0015181 A1* | 1/2006 | Elberg | A61B 17/7067 623/16.11 |
| 2006/0241601 A1* | 10/2006 | Trautwein | A61B 17/7067 606/248 |
| 2006/0293662 A1* | 12/2006 | Boyer | A61B 17/7065 606/249 |
| 2008/0140207 A1* | 6/2008 | Olmos | A61B 17/025 623/17.16 |
| 2008/0183211 A1* | 7/2008 | Lamborne | A61B 17/842 606/249 |
| 2009/0005819 A1 | 1/2009 | Ben-Mokhtar et al. | |
| 2010/0036419 A1 | 2/2010 | Patel et al. | |
| 2010/0106190 A1 | 4/2010 | Linares | |
| 2011/0022090 A1 | 1/2011 | Gordon et al. | |
| 2011/0160861 A1* | 6/2011 | Jimenez | F16H 25/20 623/17.16 |
| 2011/0172709 A1 | 7/2011 | Lyons et al. | |
| 2011/0218572 A1 | 9/2011 | Lechmann et al. | |
| 2011/0224731 A1 | 9/2011 | Smisson, III et al. | |
| 2011/0319936 A1 | 12/2011 | Gordon et al. | |
| 2012/0016418 A1 | 1/2012 | Chin et al. | |
| 2012/0053634 A1 | 3/2012 | Laskowitz et al. | |
| 2012/0059474 A1 | 3/2012 | Weiman | |
| 2012/0109198 A1 | 5/2012 | Dryer et al. | |
| 2012/0136390 A1 | 5/2012 | Butler et al. | |
| 2012/0150228 A1 | 6/2012 | Zappacosta et al. | |
| 2012/0191135 A1 | 7/2012 | Abdou | |
| 2012/0022105 A1 | 8/2012 | Ingalhalikar | |
| 2012/0221050 A1 | 8/2012 | Ingalhalikar et al. | |
| 2012/0226314 A1 | 9/2012 | Chin et al. | |
| 2013/0012996 A1 | 1/2013 | Zamani et al. | |
| 2013/0072979 A1 | 3/2013 | Butler et al. | |
| 2013/0079880 A1* | 3/2013 | Wolters | A61B 17/7055 623/17.16 |
| 2013/0103088 A1 | 4/2013 | Karahalios et al. | |
| 2013/0144339 A1 | 6/2013 | Choi et al. | |
| 2013/0158604 A1 | 6/2013 | Okamoto | |
| 2013/0184754 A1 | 7/2013 | Taber et al. | |
| 2013/0204301 A1 | 8/2013 | Mitchell et al. | |
| 2013/0211526 A1 | 8/2013 | Alheidt et al. | |
| 2013/0226240 A1 | 8/2013 | Abdou | |
| 2014/0081331 A1 | 3/2014 | Zappacosta et al. | |
| 2014/0121705 A1 | 5/2014 | Abdou | |
| 2014/0188170 A1 | 7/2014 | Zappacosta et al. | |
| 2014/0194930 A1 | 7/2014 | Hess et al. | |
| 2014/0277143 A1 | 9/2014 | Zappacosta | |
| 2015/0148844 A1 | 5/2015 | Zappacosta et al. | |

\* cited by examiner

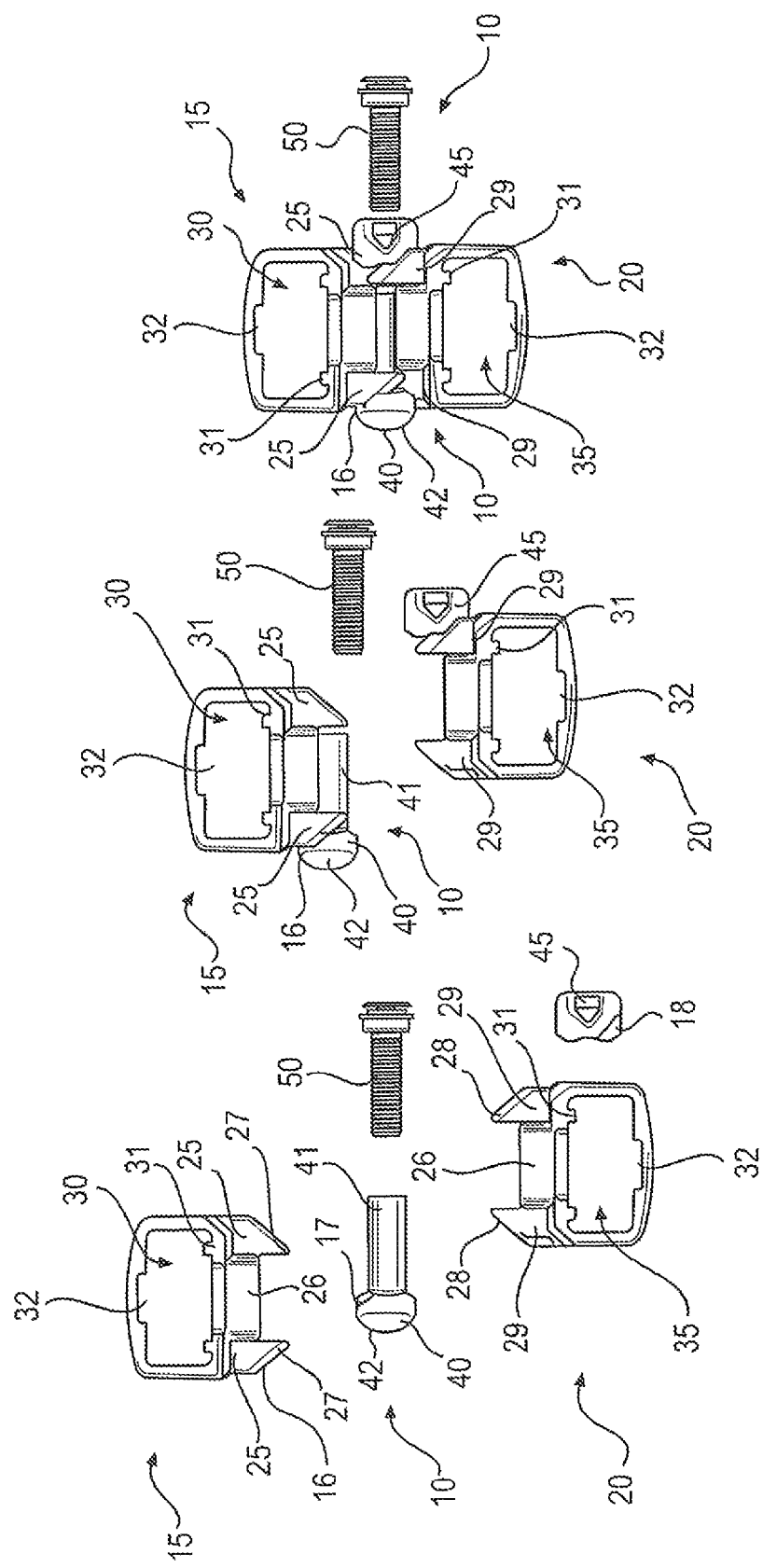

SPINOUS PROCESS FIXATION SYSTEM AND METHODS THEREOF

CROSS-REFERENCE TO RELATED APPLICATIONS

The present application is a continuation application of U.S. patent application Ser. No. 15/634,273, filed on Jun. 27, 2017 (published as U.S. Pat. Pub. 2017-0290612), which is a continuation application of U.S. patent application Ser. No. 15/364,855, filed on Nov. 30, 2016 (now issued as U.S. Pat. No. 9,724,134), which is a continuation application of U.S. patent application Ser. No. 14/989,919, filed on Jan. 7, 2016 (now issued as U.S. Pat. No. 9,539,032), which is a continuation application of U.S. patent application Ser. No. 14/090,780, filed Nov. 26, 2013 (now issued as U.S. Pat. No. 9,259,249), all of which are hereby incorporated by reference in their entirety.

FIELD OF THE INVENTION

This description relates to medical devices and systems and more particularly to a spinous process fixation system and methods thereof. In particular, in one or more implementations, this description relates to spinous process fusion devices that distract and/or immobilize the spinous processes of adjacent vertebrae.

BACKGROUND

A variety of medical devices and medical device systems may be implanted within a body of a patient to provide support to a portion or portions of the patient's body. For example, some medical devices may be implanted and coupled to backbones or portions of a spine of a patient and may be configured to provide support to the spinal bone structure of the patient.

Typically, weaknesses in the spine are corrected using devices that fuse one or more vertebrae together. It may be desirable to have an implantable device that provides for structural stability to adjacent vertebrae and to achieve supplemental fusion to treat weaknesses in the spine due to degenerative disc disease, spondylolisthesis, trauma (i.e., fracture or dislocation), tumor and/or other causes.

SUMMARY

According to one generally aspect an implantable device may be provided. The implantable device may comprise an upper assembly comprising a ramped base and a pair of opposing windows. The pair of opposing windows may extend upward from either lateral side of the ramped base. A gripping assembly may be disposed in each window. The implantable device may further comprise a lower assembly comprising a ramped base and a pair of opposing windows. The pair of opposing windows may extend down from either lateral side of the ramped base. A gripping assembly is disposed in each window. The implantable device may further comprise a ramped actuator assembly disposed between the upper assembly and the lower assembly. The ramped actuator may be configured to transition the implantable device from a collapsed form having a first height to an expanded form having a second height and wherein the second height is greater than the first height.

According to another general aspect a method of implanting a medical device may be provided. The method may comprise inserting a medical device between adjacent spinous processes. The method may further comprise rotating a central screw disposed in the medical device between an upper assembly and a lower assembly to cause the medical device to expand from a collapsed form having a first height to an expanded form having a second height. The method may further comprise clamping the medical device onto a first spinous process. The clamping may comprise extending spike plate assemblies inward to engage the first spinous process. The spike plate assemblies may be disposed in a window that extends from the upper assembly. The method may further comprise clamping the medical device onto a second spinous process. The clamping may comprise extending spike plate assemblies inward to engage the second spinous process. The spike plate assemblies may be disposed in a window that extends from the lower assembly.

According to yet another general aspect a method of assembling an implantable device may be provided. The method may comprise coupling an actuator assembly to an upper assembly and a lower assembly. The actuator assembly may be disposed between the upper assembly and the lower assembly. The actuator assembly may be configured to transition the implantable device from a collapsed form having a first height to an expanded form having a second height and wherein the second height is greater than the first height. The method may further comprise installing a gripping assembly into each of a pair of opposing windows that extend upward from the upper assembly. The method may further comprise installing a gripping assembly into each of a pair of opposing windows that extend down from the lower assembly.

The details of one or more implementations are set forth in the accompanying drawings and the description below. Other features will be apparent from the description and drawings, and from the claims.

BRIEF DESCRIPTION OF THE DRAWINGS

FIGS. 5-7 illustrate assembly of a medical device according to an example implementation.

FIG. 12a is a cut-away of the interference that binds the medical to the subassembly and spike plate according to an example implementation.

FIG. 12b is a close-up up view of a portion of the medical device of the medical device of FIG. 12a.

DETAILED DESCRIPTION

Figure 1:
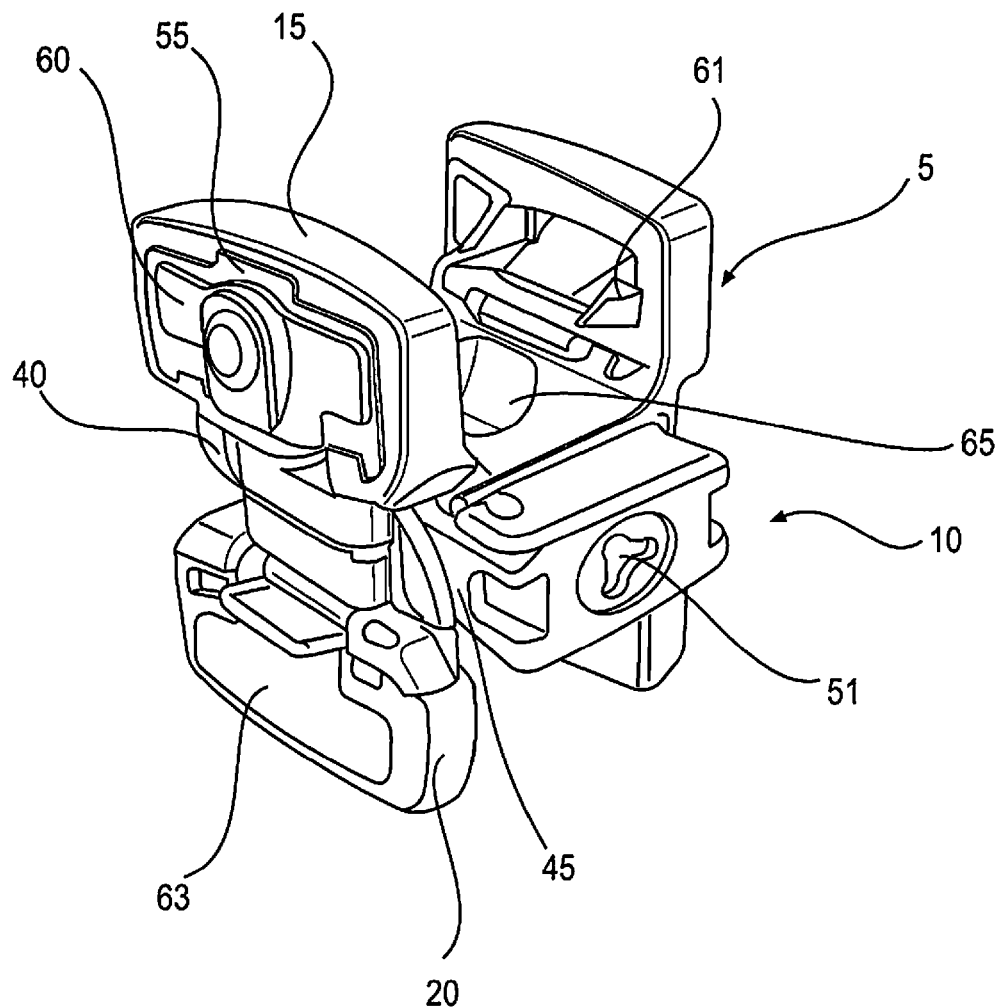
FIG. 1 is a perspective view of a medical device according to an example implementation.

Detailed implementations of the present invention are disclosed herein; however, it is to be understood that the disclosed implementations are merely examples of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but rather to provide an understandable description of the invention.

The terms "a" or "an," as used herein, are defined as one or more than one. The term "another," as used herein, is defined as at least a second or more. The terms "including" and/or "having", as used herein, are defined as comprising (i.e., open transition).

The devices and methods described herein are generally directed to medical devices that can be used to support, stabilize and/or replace anatomical structures within a body of a patient. In some implementations, the devices and methods described herein are configured to provide support to a spine or back of a patient, including providing support between two vertebrae in the spine or back of the patient. In other implementations, other portions of the body of the patient can be supported by the devices described herein.

The medical devices described herein may be implanted within a body of a patient to assist in maintaining normal physiologic motion in the spine of the patient.

The term patient may be used hereafter for a person who benefits from the medical device or the methods disclosed in the present invention. For example, the patient may be a person whose body receives the medical device disclosed by the present invention in a surgical treatment. For example, in some embodiments, the patient may be a human female, human male, or any other mammal.

This document describes implementations of an implantable medical device that may be used as a posterior, non-pedicle supplemental fixation device for use in the non-cervical spine. The medical device may be used as an interspinous fusion device. The medical device may be implanted after the removal of the supraspinous ligament. The medical device may be attached firmly to the spinous processes above and below an interspinous space. The medical device may immobilize a lumbar motion segment posteriorly with no other devices implanted. The medical device may withstand compressive, torsional and shear loads seen in the lumbar spine. The medical device may be used to achieve supplemental fusion and to treat conditions of the spine such as, for example, degenerative disc disease, spondylolisthesis, trauma (i.e., fracture or dislocation), tumor and/or other conditions.

This document describes implementations of an implantable medical device, where the medical device may include an expandable assembly that typically comprises an upper and lower assembly. The upper and lower assembly may include a multitude of windows wherein a gripping assembly may be positioned. The gripping assembly may comprise a telescoping subassembly and spike plates. Projections (e.g., spikes) that bite into the spinous process to clamp the device in place may be located on the spike plate. The expandable assembly may provide interspinous distraction, off-loading the spikes on the spike plate and reducing the chances of breaking the spinous process. The expandable assembly may be sized to fit into the interspinous space without resistance and then expanded. The expandable assembly may include a graft window anteriorly and posteriorly and may be packed with graft material after expansion using the posterior window.

Figure 2:
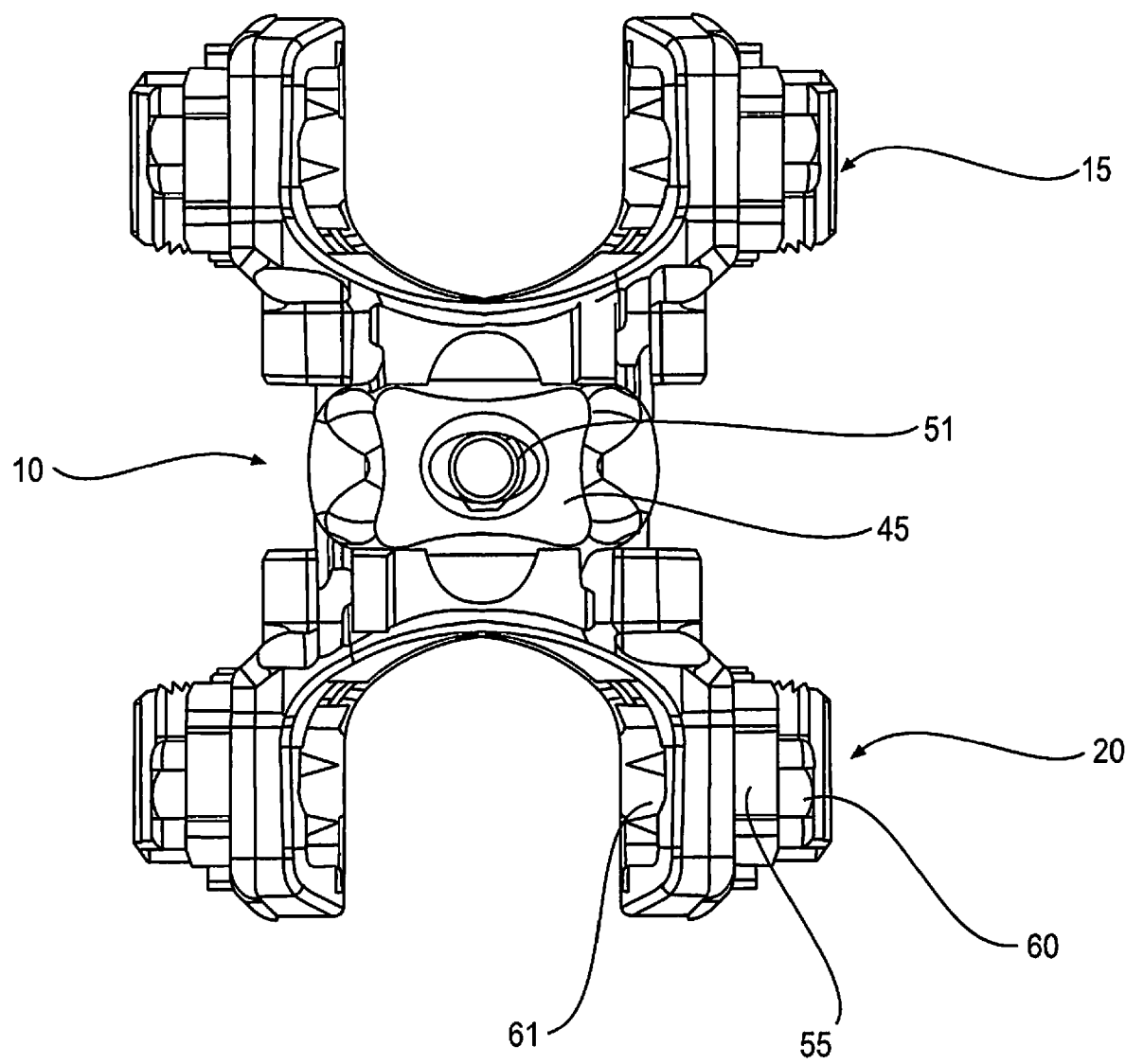
FIG. 2 is a front view of the medical device of FIG. 1.
Figure 3:
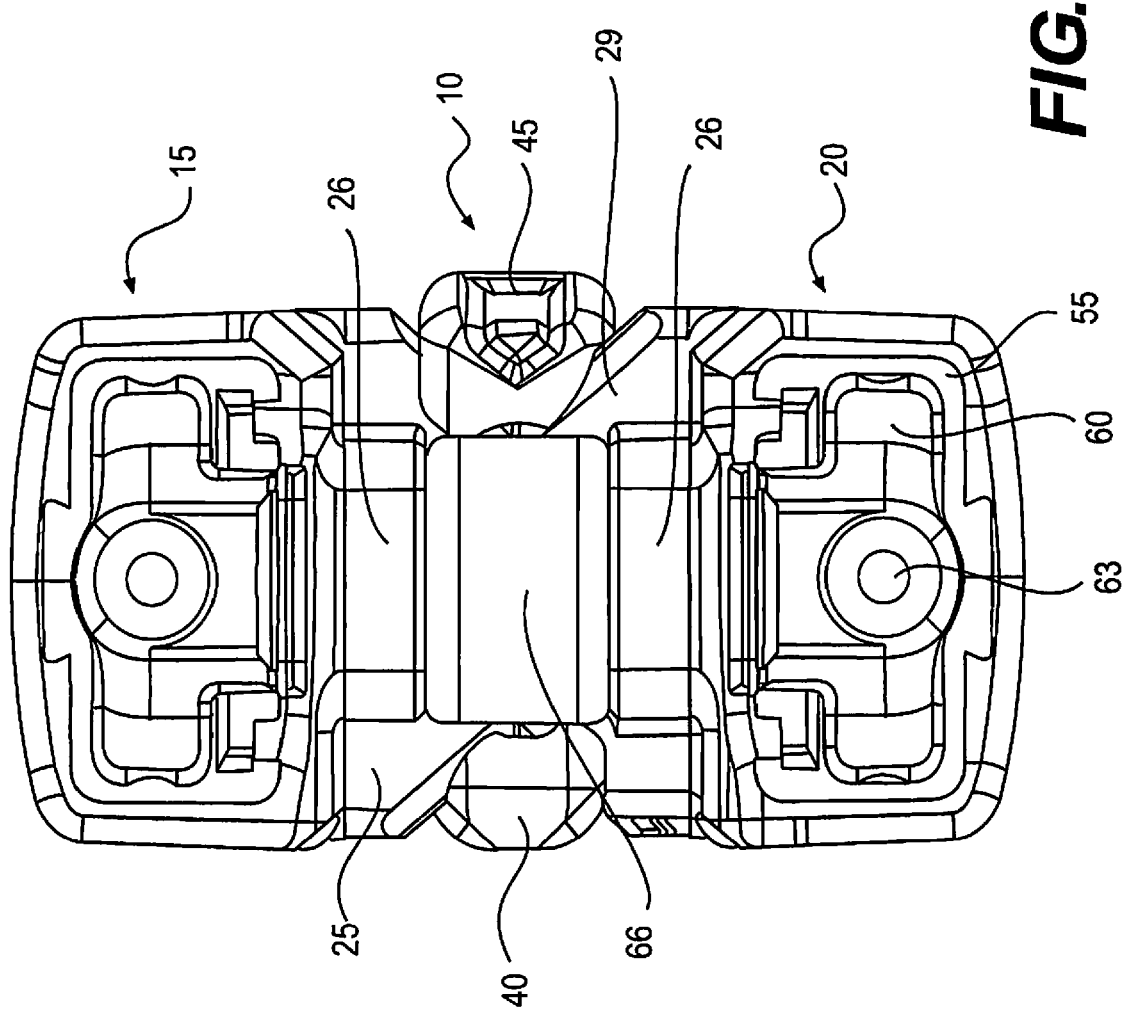
FIG. 3 is a side view of the medical device of FIG. 1.
Figure 4:
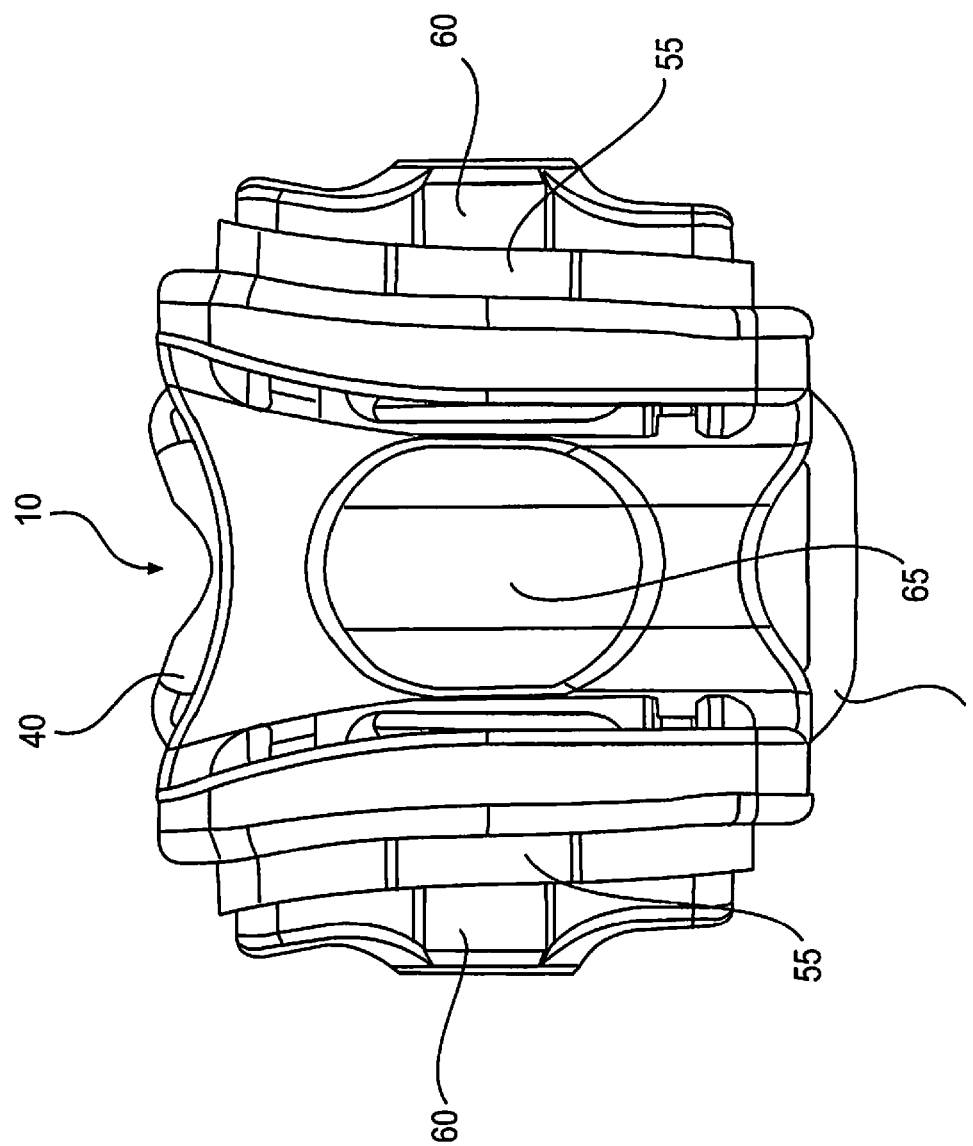
FIG. 4 is an upper view of the medical device of FIG. 1.

FIG. 1 illustrates a perspective view of a medical device 5 according to one example implementation. FIGS. 2, 3, and 4 illustrate a front view, side view, and upper view respectively, of medical device 5. As illustrated, medical device 5 may comprise an actuator assembly 10, an upper assembly 15, and a lower assembly 20. In the illustrated embodiments, medical device 5 is shown in a collapsed or contracted position with spikes 61 in a retracted position. In accordance with present embodiments, medical device 5 may be implanted in a patient and referred to as a spinous process fusion device. After insertion, medical device 5 may be expanded from the collapsed position having a first height to an expanded position having a second height, wherein the second height is greater than the first height. Spikes 61 may then be extended to clamp on the spinous process of adjacent vertebrae. In one example implementation, the maximum expanded height of the device may be about 4 mm greater than the collapsed height or, alternatively, about 6 mm greater than the collapsed height. The expansion of medical device 5 may provide interspinous distraction and may offload the forces of spikes 61 to reduce the chances of breaking a spinous process. Medical device 5 may be inserted, laterally or posteriorly, in a smaller height and then expanded to provide distraction, eliminating forces on the spinous process and potential frustration for a surgeon performing the implantation.

With additional reference to FIGS. 5-7, medical device 5 will now be described in more detail. As illustrated, medical device 5 may have several distinctive parts. For example, medical device 5 may include an actuator assembly 10, an upper assembly 15, and a lower assembly 20. FIG. 5 illustrates the parts that may be included in actuator assembly 10, which may include a front ramped actuator 40, a rear ramped actuator 45, and a central screw 50. Combining upper assembly 15 and lower assembly 20 with actuator assembly 10 forms medical device 5 in accordance with particular embodiments.

As best seen on FIGS. 5-7, upper assembly 15 may typically include a base 16 that comprises angled wedges 25, grooves 27, and a central space 26 (hereafter referred to as "pocket"). Base 16 may comprise pocket 26 flanked on both sides by angled wedges 25. In the illustrated embodiment, base 16 comprises a pair of angled wedges 25 that slope in opposite directions. A window 30 may extend vertically from base 16. Upper assembly 15 may be formed of a single piece or two or more components, which may be individually formed and combined to create upper assembly 15. Lower assembly 20 may be generally identical and formed in the same manner as upper assembly 15. Embodiments of the upper and lower assemblies 15, 20 may be shaped in a lordotic profile to match the lumbar anatomy. As discussed in more detail below, both upper and lower assemblies 10, 15 may move vertically along the axis of medical device 5. Upper assembly 15 and lower assembly 20 may each possess window 30 and 35, respectfully. Opposite each window may be an identical window 30 and 35, which may extend opposite of base 16, as best seen on FIG. 8. Both upper assembly 15 and lower assembly 20 typically comprise two windows 30 and 35 opposite each other, which each extend vertically on either lateral side of the base 16.

Medical device 10 may further include an actuator assembly 10 (best seen on FIGS. 5-7) for raising and lowering upper assembly 15 and lower assembly 20. Actuator assembly 10 may be disposed between upper assembly 15 and lower assembly 20. As illustrated, actuator assembly 10 may comprise a front ramped actuator 40, a rear ramped actuator 45, and a central screw 50. First ramped actuator 40 may be bullet shaped on its front end to facilitate insertion into a patient. Front ramped actuator 40 may possess an extension portion 41 that extends from a ramped expansion portion 42.

Ramped expansion portion 42 may be located at a front end of medical device 5 with extension portion 41 extending from ramped expansion portion 42 towards a rear end of medical device 5. Central screw 50 may extend through medical device 5 and engage extension portion 41, which may be a threaded sleeve, for example. Wedges 25, 29 of the upper and lower assemblies 15, 20, respectively, may slidingly engage ramped expansion portion 42. For example, ramped expansion portion 42 may engage wedges 25, 29 at a front end of medical device 5. Ramped expansion portion 42 may have dovetail connections with wedges 25, 29, respectively. Rear ramped actuator 45 may be disposed at a rear end of medical device 5. Wedges 25, 29 of upper and lower assemblies 15, 20 may slidingly engage rear ramped actuator 45. Rear ramped actuator 45 may have dovetail connections with wedges 25, 29, respectively. Central screw 50 may extend through rear ramped actuator 45 to engage extension portion 41.

With continued reference to FIGS. 5-7, assembly of upper and lower assemblies 15, 20 with actuator assembly 10 will be described according to one example implementation. As illustrated by FIG. 5, actuator assembly 10 may comprise a front ramped actuator 40, a rear ramped actuator 45, and a central screw 50. Upper assembly 15 may comprise spaced wedges 25, which each may comprise grooves 27. Lower assembly 15 may comprise spaced wedges 25, which each also may comprise grooves 28. Grooves 27, 28 in upper and lower assemblies 15, 20 may be linked to corresponding grooves 27, 28 in front ramped actuator 40 and rear ramped actuator 45, respectively. In FIG. 6, upper assembly 15 may be slid onto front ramped actuator 40. As illustrated, wedge 25 may engage ramped expansion portion 42 (e.g., through a dovetail connection). As further illustrated by FIG. 6, lower assembly 20 may be slide onto rear ramped actuator 45. In the illustrated embodiment, rear ramped actuator 45 may engage wedge 29 of lower assembly 20 (e.g., through a dovetail connection). In FIG. 7, upper assembly 15 may then be slid onto rear ramped actuator 45, for example, with wedge 25 engaging rear ramped actuator 45 via a dovetail connection. As further illustrated, front ramped actuator 40 also may be slid onto lower assembly 20, for example, with expansion portion 42 engaging wedge 29 via dovetail connection. After upper assembly 15 and lower assembly 20 may be attached to first and rear ramped actuators 40, 45, central screw 50 may be inserted through rear ramped actuator 45. In particular embodiments, central screw 50 may be thread into extension portion 41. FIG. 7 illustrates upper assembly 15 and lower assembly 20 coupled to actuator assembly 10 in a non-expanded position.

Figure 8:
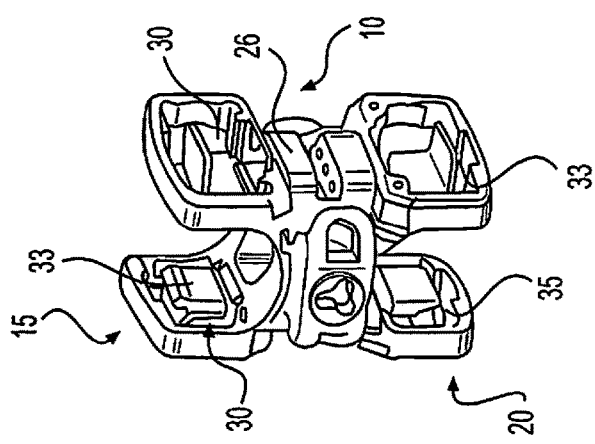

With reference now to FIGS. 8-11, insertion of gripping assembly 52 into windows 30 and 35 will now be described in accordance with one implementation. As illustrated by FIG. 8, upper assembly 15 may comprise a pair of opposing windows 30, and lower assembly 20 may also comprise a pair of opposing windows 35. Windows 30 and 35 of upper and lower assemblies 15 and 20 may each be configured to receive a corresponding gripping assembly 52, as best seen on FIG. 9. Gripping assemblies 52 may each include a telescoping subassembly 55 and spike plate assembly 60. Multiple projections 61 (hereafter referred to as "spikes") may be inserted in each spike plate assembly 60. Spike plate assembly 60 may attach to telescoping subassembly 55 through an area of interference, explained in more detail below. Likewise, telescoping subassembly 55 may attach to either window 30 or 35 through a similar area of interference. Windows 30 and 35 allow for the insertion of gripping assembly 52. The gripping assemblies 52 may move inward with respect to the windows 30 to clamp the spikes 61 onto the spinous processes. The spike plate assembly 60 may be configured to move inward toward the opposing window 30 or 35 a selected distance. The spike plate assembly 60 may travel a portion of the selected distance with the telescoping subassembly 55 and other portion of the distance without the telescoping subassembly 55.

Figure 9:
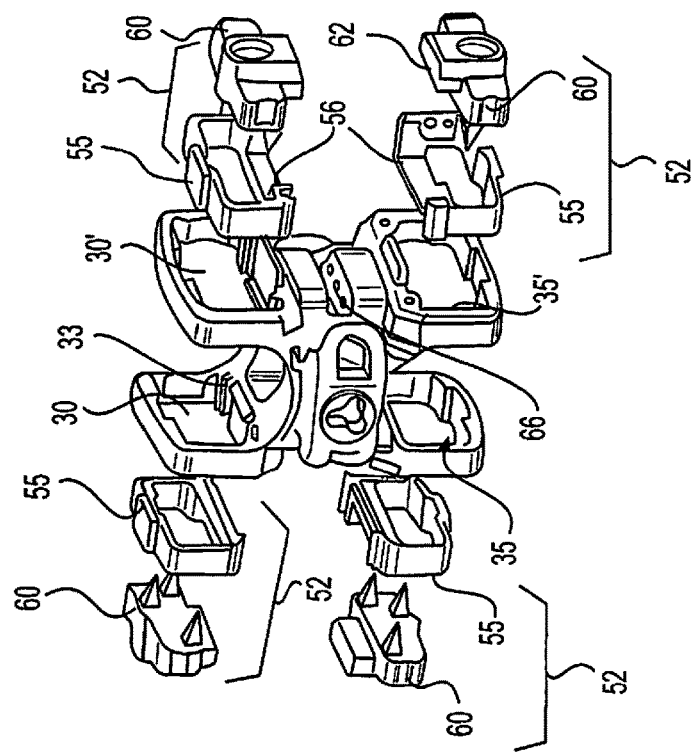
FIGS. 8-10 illustrate assembly of a subassembly and spike plate into a medical device according to an example implementation.

Telescoping subassembly 55, as illustrated in FIG. 9, may snap into the corresponding window 30 or 35. The telescoping subassembly 55 may be configured to extend inward from the corresponding window 30 or 35. By way of example, telescoping subassembly 55 may traverse up to 3 mm along rails 31 (best seen on FIGS. 5-7), positioned in windows 30 and 35. Telescoping subassembly 55 may be held in place when moving along rails 31 by a dove tail groove 32 (best seen on FIGS. 5-7), located along an outer edge of windows 30 and 35. Telescoping subassembly 55 may move freely along rails 31 but may be restricted, in some embodiments, from moving more than 3 mm inward by stoppers located at the end of rails 31 closest to actuator assembly 10.

Figure 10:
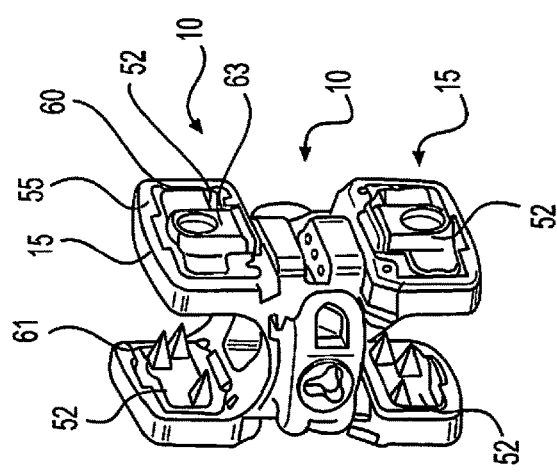
Figure 12:
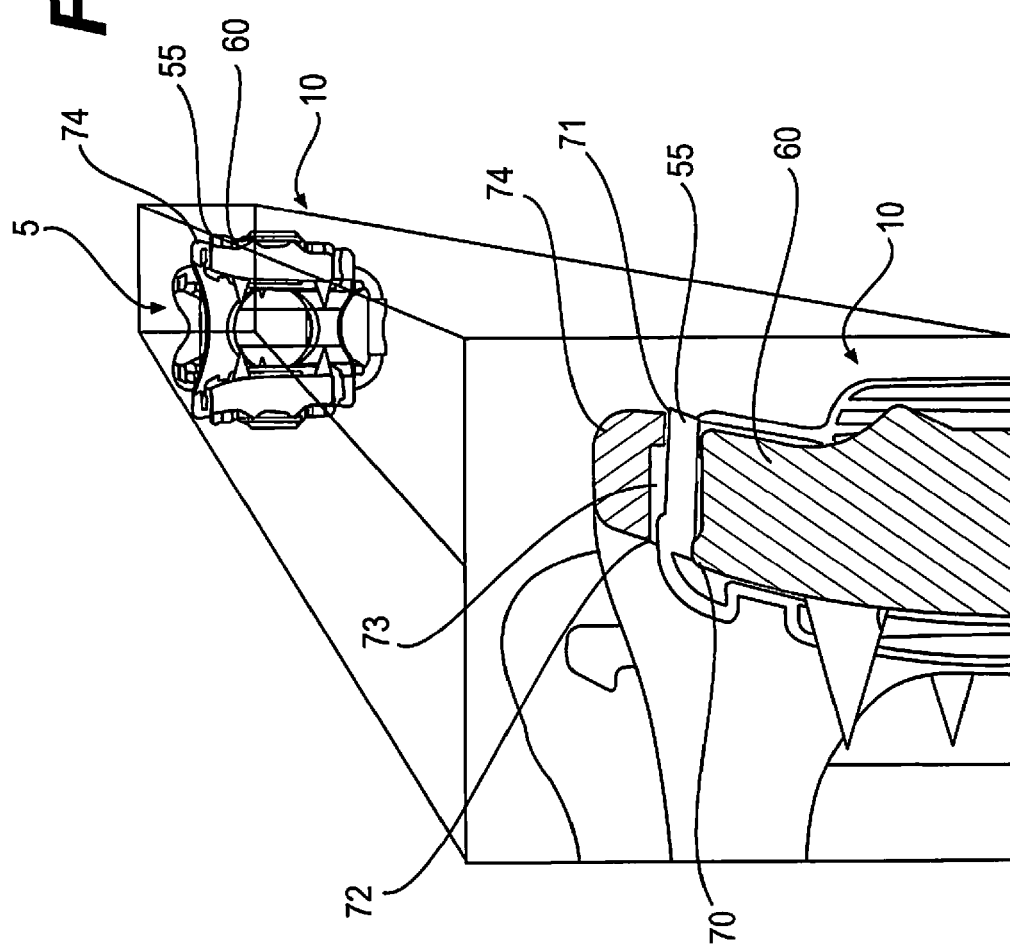

As illustrated by FIG. 9, telescoping subassembly 55 may allow for a spike plate assembly 60 that may include multiple spikes 61 to be inserted into both upper and lower assemblies 15 and 20. In particular embodiments, spike plate assembly 60 may be snapped into telescoping subassembly 55 in a similar manner to attachment of telescoping subassembly 55 to either upper assembly 15 or lower assembly 20. FIG. 10 illustrates gripping assemblies 52 disposed in upper and lower assemblies 15 and 20, respectively. As illustrated, spike plate assembly 60 is also disposed in telescoping subassembly 55. In FIGS. 12a and 12b, a cut-away view of an example embodiment of medical device 5 illustrates upper assembly 15, subassembly 55, and spike plate assembly 60 attached to one another. As illustrated, an interference 70 (e.g., flange) formed on the spike plate assembly 60 snaps into a groove 71 in telescoping subassembly 55. After interference 70 is snapped into groove 71, spike plate assembly 60 cannot be slid back out. As further illustrated, telescoping subassembly 55 may be secured in window housing 74 in a similar manner. By way of example, telescoping subassembly 55 may comprise an interference 72 (e.g., flange) that snaps into a groove 73 in window housing 74. After interference 72 is snapped into groove 73, telescoping subassembly 55 cannot be slid back out.

Figure 11:
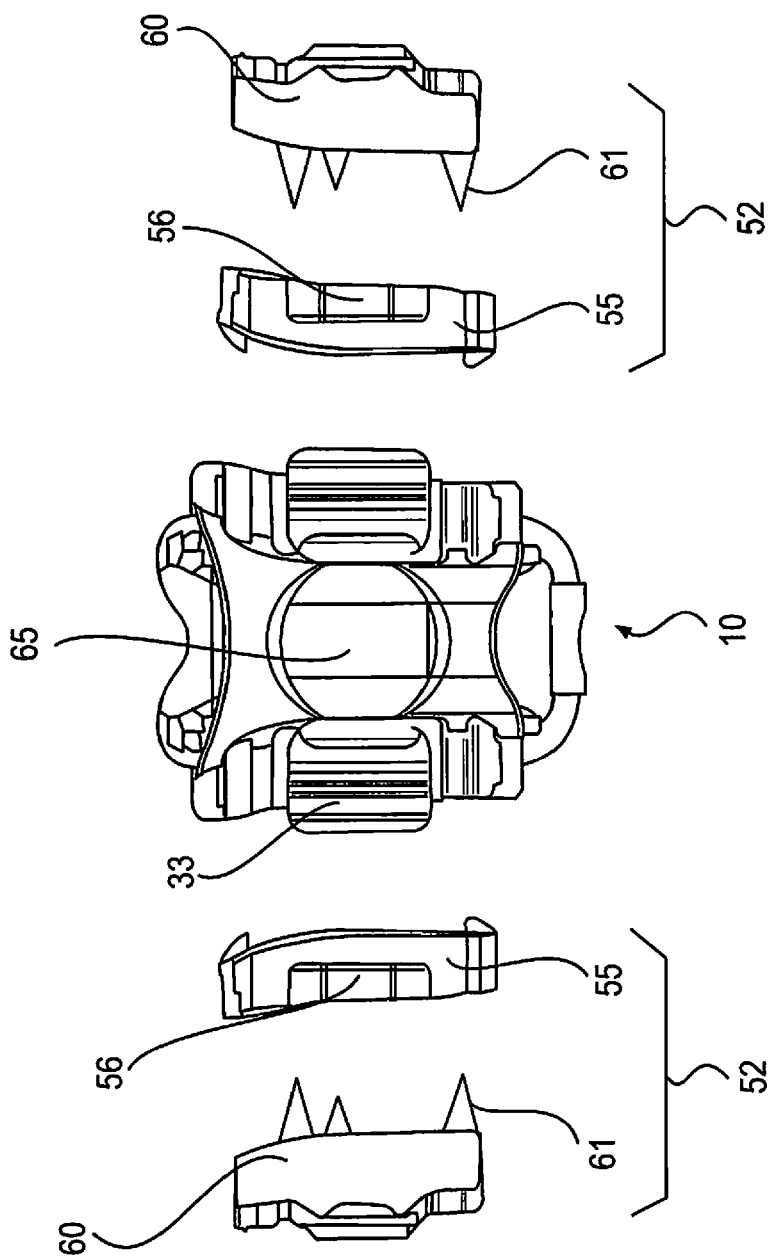
FIG. 11 is an upper view cut-away of the medical device of FIG. 8.

Once assembled, spike plate assembly 60 may move up to 3 mm, for example, inside telescoping subassembly 55 as it traverses down cut-out 56, as seen in FIGS. 9 and 11. Cut-out 56 in telescoping assembly 55 may prevent spike plate assembly 60 from rotating or twisting, in accordance with certain embodiments. As seen in FIG. 9, each spike plate assembly 60, in some embodiments, may contain rows of teeth 62 that connect to ratchet mechanism 33. Ratchet mechanism 33, illustrated in FIG. 8, may be an "L" shaped component with an opposing set of teeth cut into it. Ratchet mechanism 33 may be positioned and secured inside pocket 26 (e.g., FIG. 8). The row of teeth on ratchet mechanism 33 secure it to pocket 26. Both sets of teeth on spike plate assembly 60 and ratchet mechanism 33 may be designed to interact with each other. Teeth 62 and ratchet mechanism 33 may allow spike plate assembly 60 and telescoping subassembly 55 to move forward but not backwards. This may allow for spikes 61 on spike plate assembly 60 to clamp to a spinous process without fear of release. Movement along ratchet mechanism 33 may be facilitated by a round depression 63 located on the back of spike plate assembly 60, as illustrated by FIGS. 9 and 10. A tool, not pictured, may be configured to fit into depression 63 helping medical personnel push spike plate assembly 60 along ratchet mechanism 33.

While spikes 61 are shown with a sharp, pointed, projection, suitable spikes may possess a more tapered point, rounded point, or other type of ending to the projection. Spikes 61, pictured in FIGS. 8-10, may be used to attach firmly and bite into the spinous processes above and below an interspinous space. Spikes 61 may be integrally formed with spike plate assembly 60 or spikes 61 may be separate components that are secured to spike plate assembly 60. Spikes 61 may be pyramid shaped with a base portion secured or integrally formed on spike plate assemblies 60. The sides of spikes 61 may extend from the base to form a point in the shape of a pyramid. In other example implementations, spikes 61 may be formed into other shapes that rise to a point to enable the spike to engage the spinous process. As discussed above, the end of spikes 61 may include tips other than a point such as, for example, a rounded tip, a square tip or other-shaped tip.

Spike plate assembly 60 and spikes 61 may be made of titanium. In other implementations, spike plate assembly 60 and spikes 61 may be made of other biocompatible materials. The example illustration of medical device 5 includes three (3) spikes 61 on each spike plate assembly 60. In other example implementations, fewer or more spikes 61 may be included. In one example implementation, spikes 61 on opposing portions spike plate assembly 60 may be aligned across from one another. In other example implementations, spikes 61 on opposing spike plate assemblies 60 may be offset from one another.

Figure 13:
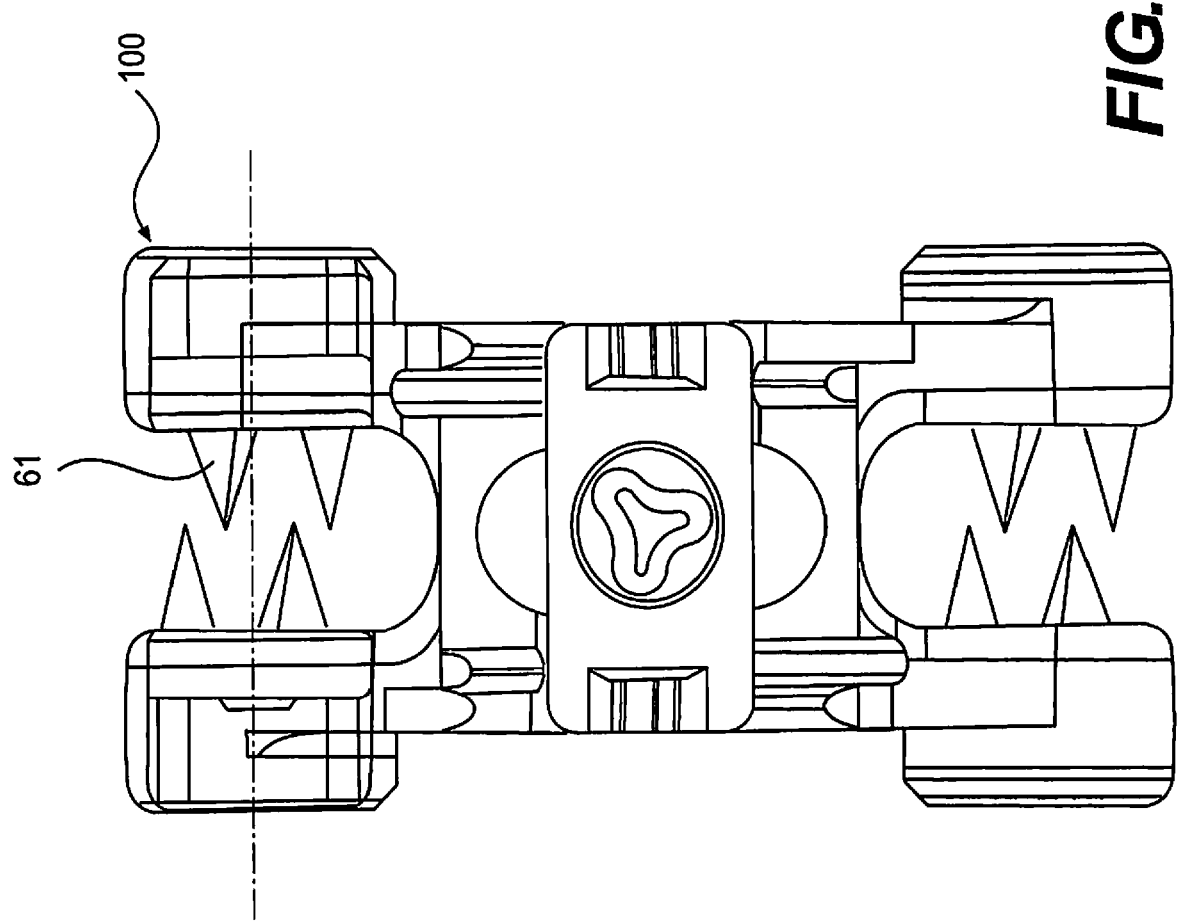
FIG. 13 is a side view of an alternate embodiment.
Figure 14:
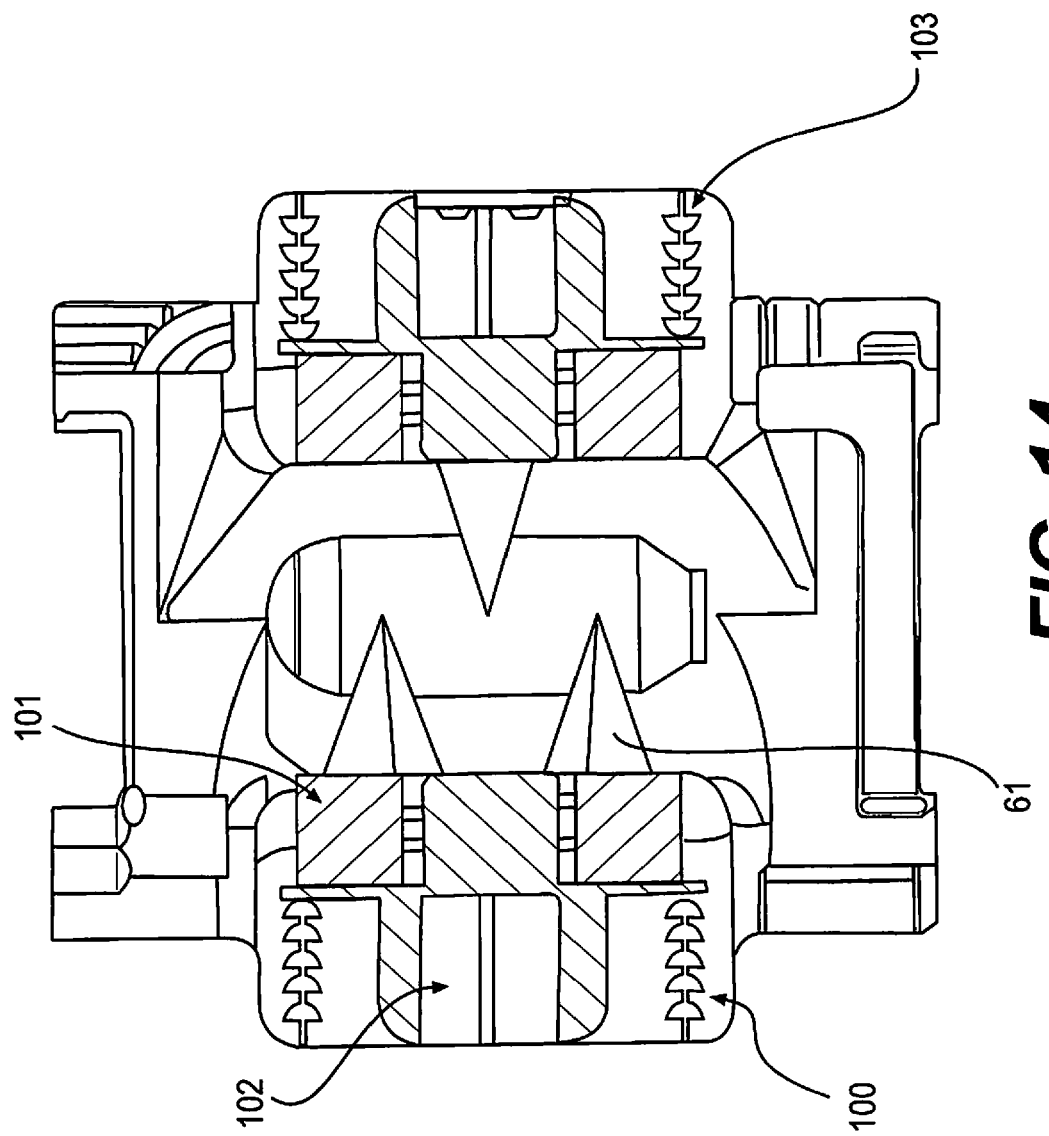
FIG. 14 is a cut-away of an alternate embodiment of the spike plate assembly.
Figure 15:
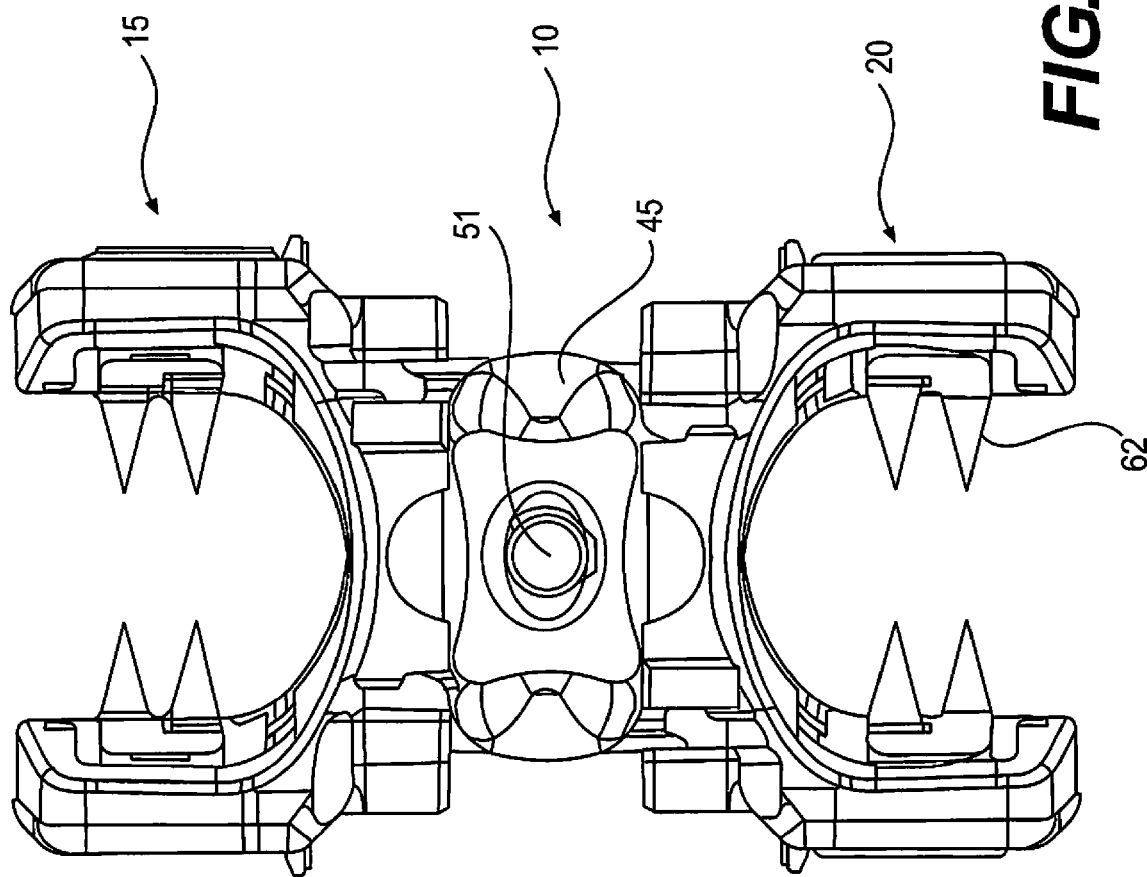
FIG. 15 is a front view of the medical device with an engaged spike plate.

A further embodiment of telescoping subassembly 55 and spike plate assembly 60 can be seen in FIGS. 13 and 14. In this embodiment both telescoping subassembly 55 and spike plate assembly 60 may be formed into a single hub/boss 100. Hub/boss 100, as seen in FIG. 15, may house a dynamic member with two components, medial member 101 and lateral member 102 which may use a hex feature to radially engage a driver and tabs. The assembly may have linear sliding motion within hub/boss 100, while the lateral member may have an additional rotational motion component. The sliding motion of the assembly enables engagement of spikes 61 with the spinous process, while the rotational motion of lateral plates 102 enables engagement and disengagement of the radial locking tabs with a ratchet 103 machined on the inside of the hub/boss 100. The locking mechanism may be used to keep spikes 61 engaged with the spinous process consists of two tabs and a ratchet on each of the dynamic members.

An embodiment for using medical device 5 will now be described in accordance with one example implementation. For example, a method may comprise inserting medical device 5 into an interspinous space. Medical device 5 may be inserted into the interspinous space a contracted position. FIG. 2 illustrates medical device 5 in a contracted position with spike plates 60 and spikes 61 in a retracted position. That is, spikes 61 are recessed within upper and lower assemblies 15 and 20. After insertion, the method may further comprise expanding medical device 5 from a collapsed form having a first height to an expanded form having a second height, where the second height is greater than the first height. In one example implementation, the maximum expanded height of medical device 5 may be about 6 mm greater than the collapsed height. Central screw 50 may be rotated to expand medical device 5 from a collapsed form to an expanded form in the interspinous space. Second ramped actuator 45 may be held in place while central screw 50 is turned causing front ramped actuator 40 to be drawn toward rear ramped actuator 45. First and rear ramped actuators 40, 45 may engage the wedges 27, 29 of upper and lower assemblies 15, 20, respectively, forcing upper and lower assemblies 15, 20 away from one another and into an expanded position. A counter rotation of central screw 50 may cause front ramped actuator 40 and rear ramped actuator 45 to separate causing upper and lower assemblies 15, 20 to collapse from the expanded state.

The process may next include clamping spikes 61 onto the spinous processes. As previously described, a tool may be used to push gripping assemblies 52 inward and place spike plate assemblies 60 and spikes 61 in an engaged position. FIG. 15 illustrates an implementation of medical device 5 with spike plate assemblies 60 and spikes 61 in the engaged position being extended inward from the window 30. The tool may be used to independently move each of gripping assemblies 52 in particular embodiments. Each spike plate assembly 60 may move a first distance until a mechanical stop is reached followed by movement of spike plate assembly 60 together with the corresponding telescoping subassembly 55 a second distance. A mechanical stop may also limit inward movement of telescoping subassembly 55 with spike plate assembly 60. After assemblies 15 and 20 are positioned along the vertical axis, spikes 61 on spike plate assemblies 60 may engage and clamp (or bite) into the spinous process. In this manner, spikes 61 positioned on upper assembly 15 may clamp into one spinous process and spikes 61 on lower assembly 20 may clamp into an adjacent spinous process.

As discussed above, medical device 5 may be expanded after insertion into the interspinous space in accordance with certain embodiments. After expansion, medical device 5 may be packed with bone graft material using openings 65 or 66, seen in FIGS. 4, 9, and 11. In the illustrated embodiment, upper assembly 15 includes a first opening 65 (e.g., also referred to as an opening or an anterior window), and lower assembly 20 include a second opening 66 (e.g., also referred to as an opening or a posterior window). First opening 65 and second opening 66 may be used as graft windows for the packing of bone graft material following the insertion and placement of medical device 5 in a patient. In one implementation, after medical device 5 has been expanded, medical device 5 may be packed with bone graft using posterior window 66. In this manner, graft containment areas accessed by windows 65 and 66 may provide for a larger grafting area and may be packed after expansion of medical device 5.

What is claimed is:

1. A method of implanting a medical device in a patient, the method comprising:
    inserting a medical device between adjacent spinous processes;
    rotating a central screw disposed in the medical device between an upper assembly and a lower assembly to cause the medical device to expand from a collapsed form having a first height to an expanded form having a second height; and
    clamping the medical device onto a first spinous process, wherein the clamping comprises extending upper spike plate assemblies inward to engage the first spinous process, each upper spike plate assembly being disposed in a window that extends from the upper assembly; and
    clamping the medical device onto a second spinous process, wherein the clamping comprises extending lower spike plate assemblies inward to engage the second spinous process, each lower spike plate assembly being disposed in a window that extends from the lower assembly, wherein the clamping the medical device onto the first spinous process further comprises extending telescoping subassemblies inward, each of the upper spike plate assemblies that engage the first spinous process being disposed in a corresponding one of the telescoping subassemblies, and wherein the upper spike plate assemblies move in the corresponding window until a respective stop is reached, wherein the telescoping subassemblies and the upper spike plate assemblies continue to extend inward along rails in the corresponding window after the stops have been reached.

2. The method of claim 1, wherein rotation of the central screw draws a front ramped actuator toward a rear ramped actuator, the front ramped actuator and the rear ramped actuator acting on the upper assembly and the lower assembly to cause the medical device to expand.

3. The method of claim 1, wherein the telescoping subassemblies are configured to traverse a selected distance upon the corresponding rails.

4. The method of claim 3, wherein each telescoping subassembly is guided on their corresponding rails by a dovetail connection.

5. The method of claim 4, wherein each upper spike plate assembly is configured to move inward toward the opposing window a selected distance.

6. The method of claim 5, wherein each upper spike plate assembly travels a portion of the selected distance with the corresponding telescoping subassembly and another portion of the distance without the corresponding telescoping subassembly.

7. The method of claim 2, wherein the upper spike plate assemblies and the lower spike plate assemblies ratchet inward.

8. The method of claim 7, wherein a ratchet mechanism engages each spike plate assembly, the ratchet mechanism being secured in a pocket in a corresponding base of the respective upper or lower assembly.

9. A surgical method comprising:
inserting an implantable device into an interspinous space, wherein the implantable device is in a collapsed form having a first height; and
expanding the implantable device in the interspinous space, wherein the implantable device is expanded to an expanded form having a second height,
wherein the implantable device comprises:
an upper assembly comprising a ramped base and a pair of opposing windows extending upward from either lateral side of the ramped base, wherein a gripping assembly is disposed in each window;
a lower assembly comprising a ramped base and a pair of opposing windows extending down from either lateral side of the ramped base, wherein a gripping assembly is disposed in each window; and
a ramped actuator assembly disposed between the upper assembly and the lower assembly and configured to transition the implantable device from a collapsed form having a first height to an expanded form having a second height and wherein the second height is greater than the first height, wherein the implantable device is configured to be clamped onto a first spinous process by extending telescoping subassemblies inward, wherein each gripping assembly in the upper assembly is disposed in a corresponding one of the telescoping subassemblies, and wherein the gripping assemblies of the upper assembly move in the corresponding window until a respective stop is reached, wherein the telescoping subassemblies and the gripping assemblies of the upper assembly continue to extend inward along rails in the corresponding window after the stops have been reached.

10. The method claim 9, wherein the ramped actuator assembly includes a front ramped actuator in engagement with the upper assembly and the lower assembly; a rear ramped actuator in engagement with the upper assembly and the lower assembly; and a central screw that extends from the rear ramped actuator through the front ramped actuator.

11. The method of claim 10, wherein the front ramped actuator and the rear ramped actuator are configured to act on the upper assembly and the lower assembly in response to rotation of the central screw.

12. The method of claim 9, wherein the ramped base of the upper assembly includes a pair of angled wedges in engagement with the ramped actuator assembly, and wherein the ramped base of the lower assembly comprises a pair of angled wedges in engagement with the ramped actuator assembly.

13. The method of claim 12, wherein the angled wedges of the upper assembly slope in opposite directions, and wherein the angled wedges of the lower assembly slope in opposite directions.

14. The method of claim 12, wherein the ramped base of the upper assembly comprises a pocket between the pair of angled wedges, and wherein the ramped base of the lower assembly comprises a pocket between the pair of angled wedges.

15. The method of claim 9, wherein at least one gripping assembly of the upper assembly and/or the lower assembly comprises spike plate assembly disposed in the telescoping assembly.

16. The method of claim 15, wherein each telescoping subassembly comprises a flange that engages the corresponding window to prevent backing out of the corresponding telescoping subassembly.

17. The method of claim 15, wherein each telescoping subassembly is configured to traverse a selected distance upon the corresponding rails.

18. The method of claim 17, wherein each telescoping subassembly is guided on the corresponding rails by a dovetail connection.

* * * * *